United States Patent
Nichols

(10) Patent No.: US 9,272,141 B2
(45) Date of Patent: Mar. 1, 2016

(54) HANDHELD FACIAL MASSAGE AND MICROCURRENT THERAPY DEVICE

(76) Inventor: Thomas Nichols, Laguna Niguel, CA (US)

( * ) Notice: Subject to any disclaimer, the term of this patent is extended or adjusted under 35 U.S.C. 154(b) by 664 days.

(21) Appl. No.: 13/173,439

(22) Filed: Jun. 30, 2011

(65) Prior Publication Data

US 2012/0165710 A1 Jun. 28, 2012

Related U.S. Application Data

(60) Provisional application No. 61/360,826, filed on Jul. 1, 2010.

(51) Int. Cl.

| A61N 1/04 | (2006.01) |
| A61H 7/00 | (2006.01) |
| A61N 1/36 | (2006.01) |
| A61H 23/02 | (2006.01) |
| A61N 1/20 | (2006.01) |
| A61N 1/32 | (2006.01) |
| A46B 7/04 | (2006.01) |
| A46B 13/00 | (2006.01) |
| A46B 13/02 | (2006.01) |

(52) U.S. Cl.
CPC .............. *A61N 1/36014* (2013.01); *A46B 7/04* (2013.01); *A46B 13/008* (2013.01); *A46B 13/02* (2013.01); *A61H 7/005* (2013.01); *A61H 23/0263* (2013.01); *A61N 1/205* (2013.01); *A61N 1/328* (2013.01); *A46B 2200/102* (2013.01); *A61H 2201/10* (2013.01); *A61H 2201/1685* (2013.01); *A61H 2205/022* (2013.01); *A61N 1/322* (2013.01)

(58) Field of Classification Search
CPC ..... A61N 1/205; A61N 1/328; A61N 1/36014; A61H 7/005; A61H 23/0263; A46B 7/04; A46B 13/008; A46B 13/02
USPC ...................... 601/73, 46, 67; 606/9; 607/2–3
See application file for complete search history.

(56) References Cited

U.S. PATENT DOCUMENTS

| 2,424,699 | A | 7/1947 | Marty ........................... 128/24.2 |
| 5,336,159 | A | 8/1994 | Cheng .............................. 601/15 |
| 6,443,915 | B1 | 9/2002 | Hwang ............................ 601/15 |
| 6,684,107 | B1 * | 1/2004 | Binder ............................. 607/72 |
| 7,194,316 | B2 | 3/2007 | Bousfield et al. ............. 607/150 |
| 7,331,964 | B2 | 2/2008 | Maricle et al. ................... 606/88 |
| 2004/0147984 | A1 | 7/2004 | Altshuler et al. ............... 647/88 |

(Continued)

FOREIGN PATENT DOCUMENTS

DE 102407 7/1991 ............. A46B 15/00

*Primary Examiner* — Justine Yu
*Assistant Examiner* — Timothy Stanis
(74) *Attorney, Agent, or Firm* — Steins & Associates, P.C.

(57) ABSTRACT

A handheld facial massage and microcurrent therapy device. The device includes a massage feature that enables the user to provide motorized agitation to a skin-contacting attachment selected from a group of detachable elements. The detachable skin-contacting element includes bristle brushes, massage sponges, smooth and rough applicators, among others. In addition to the motorized agitation from the attachment, the device also includes the ability to apply rejuvenating micro-current therapy to the skin. Both the motorized agitation and micro-current generation are independently user-adjustable in order to achieve the optimum treatment for each individual. Versions of the device that include galvanic current application as well as ultrasonic skin stimulation are available. The device is compact and easy to use so that the non-professional user can self-treat with professional results.

20 Claims, 10 Drawing Sheets

(56) References Cited

U.S. PATENT DOCUMENTS

| | | | |
|---|---|---|---|
| 2007/0123808 A1* | 5/2007 | Rhoades | 601/73 |
| 2007/0198004 A1 | 8/2007 | Altshuler et al. | 606/9 |
| 2007/0239143 A1 | 10/2007 | Altshuler et al. | 606/9 |
| 2008/0214968 A1* | 9/2008 | Milne et al. | 601/15 |
| 2010/0274329 A1* | 10/2010 | Bradley et al. | 607/90 |
| 2010/0292746 A1* | 11/2010 | Gorham | 607/3 |
| 2011/0098781 A1* | 4/2011 | Mantle et al. | 607/46 |
| 2011/0106067 A1* | 5/2011 | Geva et al. | 606/9 |

\* cited by examiner

HANDHELD FACIAL MASSAGE AND MICROCURRENT THERAPY DEVICE

This application is filed within one year of, and claims priority to Provisional Application Ser. No. 61/360,826, filed Jul. 1, 2010.

BACKGROUND OF THE INVENTION

1. Field of the Invention

This invention relates generally to portable skincare devices and, more specifically, to a Handheld Facial Massage and Microcurrent Therapy Device.

2. Description of Related Art

Life expectancy for humans continues to be extended. While many people are benefit by the benefits and enjoyment of longer lifespan, there are some aspects of the extended longevity that are not so desirable. One such aspect relates to skin condition (facial, in particular). As we age, it is generally accepted that our skin will become less and less elastic. As the skin becomes less elastic, it will tend to appear loose and less toned (generally viewed as undesirable traits).

In order to combat the attack on skin by aging, a plethora of products and treatments have been introduced. Many of these treatments are invasive, expensive and traumatic. Skin peels, laser treatments and even clinical injections are now offered by a wide variety of establishments, from Doctors' offices to tanning salons.

In addition to the institutional offerings for skin rejuvenation, a wide variety of home use products have also become available. There is a virtually unending supply of motorized brushes, massagers, lotions and treatments designed for home use.

The problem with the institutional skin treatments is that they are inconvenient and prohibitively expensive. As a result, the average individual cannot utilize their services on a daily basis.

The problem with the home use products and treatments is that none of them has risen above the others as being nearly as effective as the institutional products or services.

What is needed, then, is a skin cleaning and/or toning device that has the effectiveness of the institutionally-available treatments, but the cost and convenience of a home-use product.

SUMMARY OF THE INVENTION

In light of the aforementioned problems associated with the prior devices and assemblies, it is an object of the present invention to provide a Handheld Facial Massage and Microcurrent Therapy Device. A massage feature should be provided that enables the user to provide motorized agitation to a skin-contacting attachment selected from a group of detachable elements. The detachable skin-contacting element should include bristle brushes, massage sponges, smooth and rough applicators, among others. In addition to the motorized agitation from the attachment, the device should also include the ability to apply rejuvenating micro-current therapy to the skin. Both the motorized agitation and micro-current generation should be independently user-adjustable in order to achieve the optimum treatment for each individual. Versions of the device that include galvanic current application as well as ultrasonic skin stimulation should also be available. The device should be compact and easy to use so that the non-professional user can self-treat with professional results.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, of which:

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a Handheld Facial Massage and Microcurrent Therapy Device.

Figure 1:
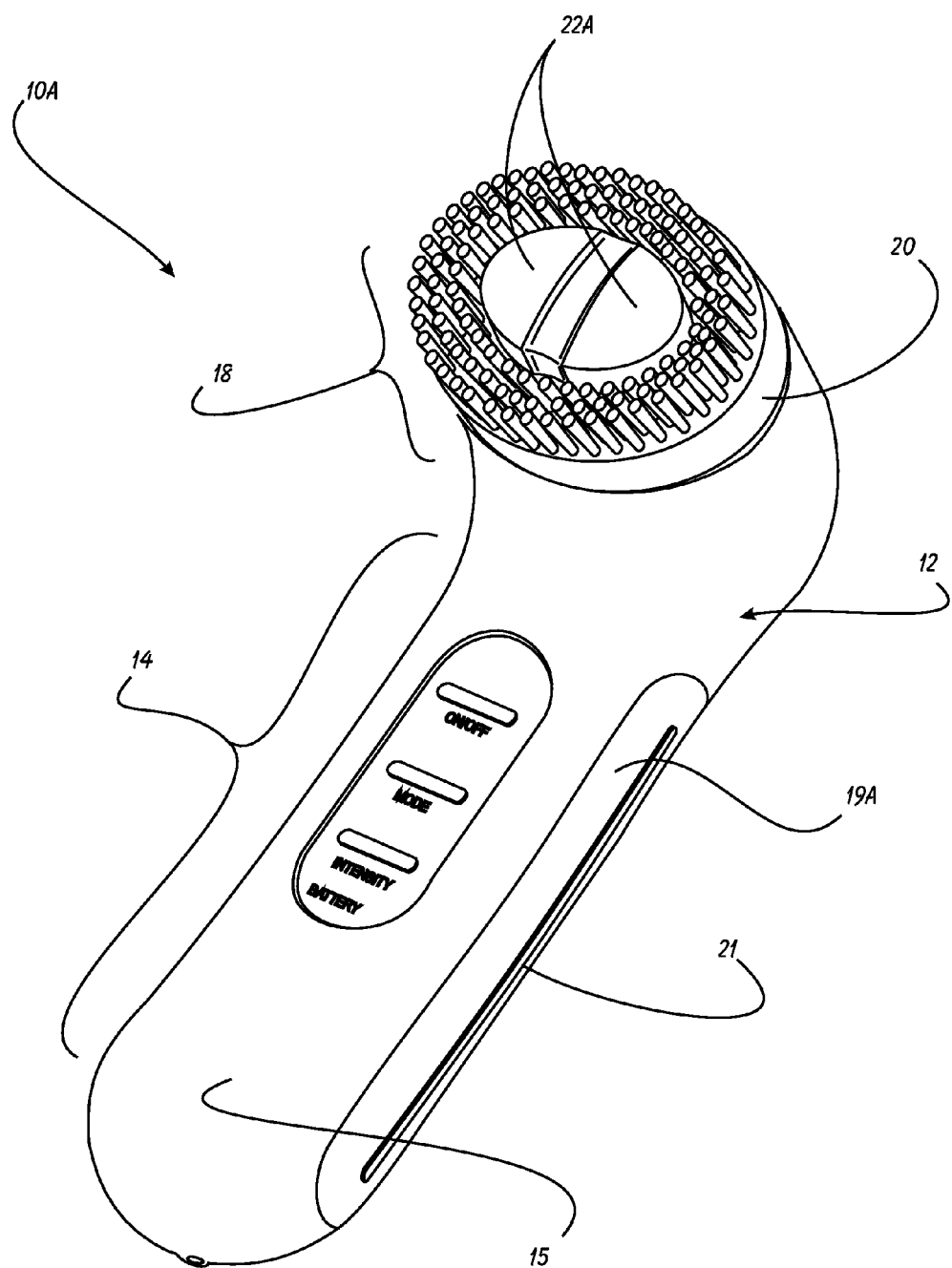
FIG. 1 is a front perspective view of a preferred embodiment of the handheld facial massage and microcurrent therapy device of the present invention.

The present invention can best be understood by initial consideration of FIG. 1. FIG. 1 is a front perspective view of a preferred embodiment of the handheld facial massage and micro current therapy device 10A of the present invention. The device 10A is specifically designed to provide the in-home user with many of the skin rejuvenating and toning benefits previously only available through doctors' offices and other institutional service-providers. To this end, the device 10A provides a hand-held power micro-pulsating vibration cleansing facial brush further equipped with the ability to apply micro-current to the user's skin. In other forms or versions, rotational/oscillating movements will also be generated by the device 10A. The device 10A is designed to cleanse and exfoliate the epidermal layer, and to provide facial toning. The device 10A preferably has a facial brush for targeting the face, neck and body to exfoliate, cleanse and provide toning to temporarily diminish fine lines and wrinkles.

The device 10A is defined by a hand-held-sized housing 12, that has a lower handle section 14, extending upwardly into a head section 18. At its lower end, the housing 12 may have a charging pads (not shown) formed therein in order to allow an external power supply to provide recharging power to internal batteries. The external power supply may come from a stand device (see FIG. 10), or counter stand, that will hold the device 10A securely when it is not in use (while at the same time recharge the batteries).

The device 10A is defined by a detachable brush unit 20 (attaches to the face of the head section 18). A current emitter face 22A protrudes through a central aperture formed in the brush unit 20, as will be described more fully below in connection with other drawing figures. It should be understood that the brush unit 20 is only one in a series of detachable units that are available for installation on the head section 18 of the device 10A. For example, the detachable unit could have facial brush bristles, a sponge or other textured or smooth substrates. In the depicted version, there are a plurality of brush bristles 24 extending upwardly from a peripheral base unit 25.

The face of the skin-contacting surface of the detachable unit 20 and the current emitter face 22A are cooperatively designed (when the detachable unit 20 is installed) to both engage the user's skin surface with even contact over the skin area to be treated.

The housing 12 is defined by a front face 15 that has a plurality of control/display elements that are more fully described below. The housing 12 is further preferably water resistant (or even "waterproof"). Conductor ridges 21 are located on opposing sides (preferably) of the housing 12. These conductor ridges 21 have metallic surfaces, and are located as such on the handle section 14 so that the user will be placing his or her hand over them when grasping the device 10A. These conductor ridges 21 provide electrical conductivity between the skin of the user and the micro-current circuitry when the user grasps the device 10A normally. This connectivity provides the necessary polarity to permit the current emitter face 22A to emit micro-currents into the user's skin. Grip pads 19A are positioned around the conductor ridges 21 in order to aid the user in grasping the device 10A and to prevent its slipping out of the user's hand (such as if the device surface is wet). If we now turn to FIG. 2, we can continue to examine the details of this new and impressive device.

Figure 2:
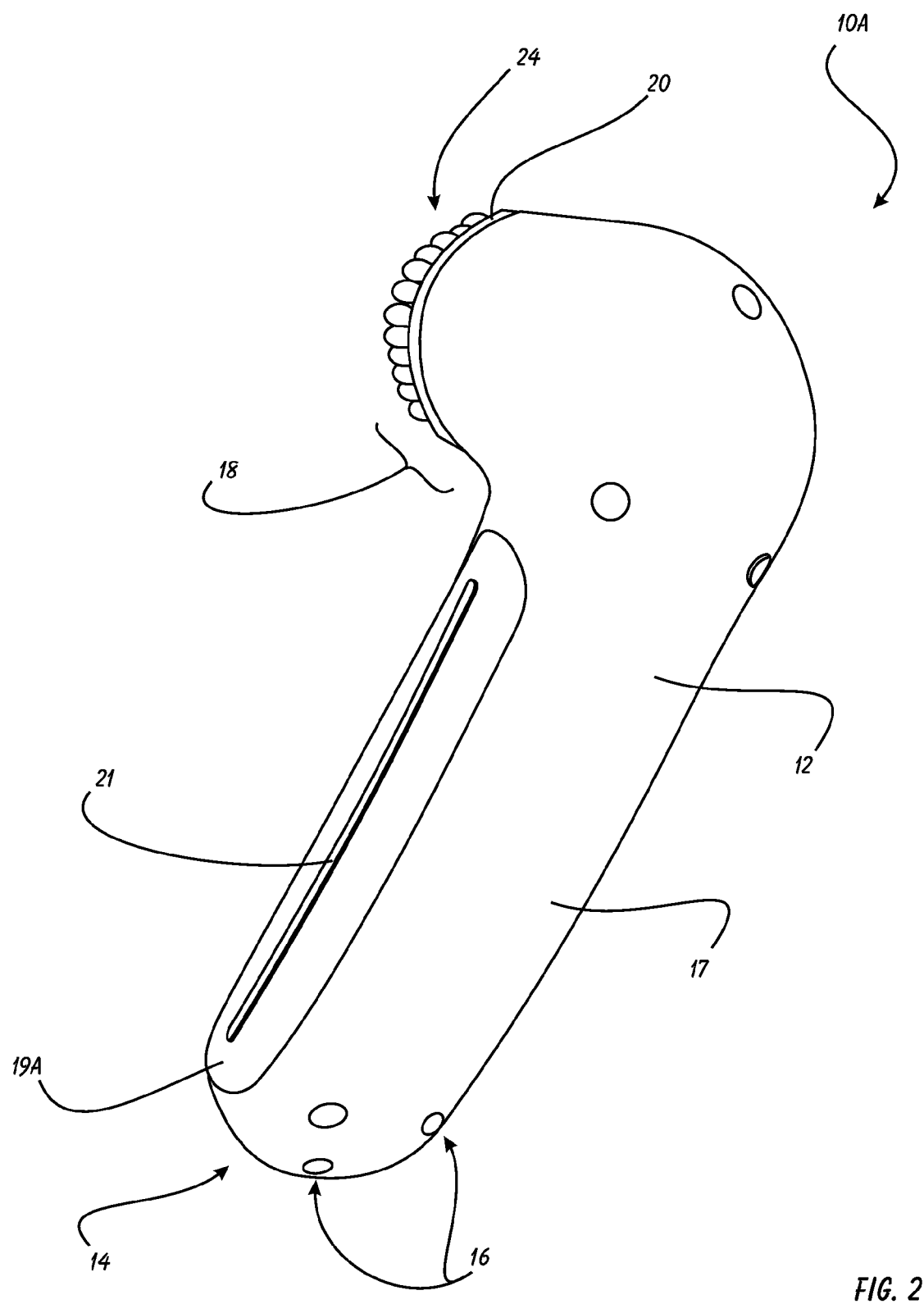
FIG. 2 is a rear perspective view of the device of FIG. 1.
Figure 3:
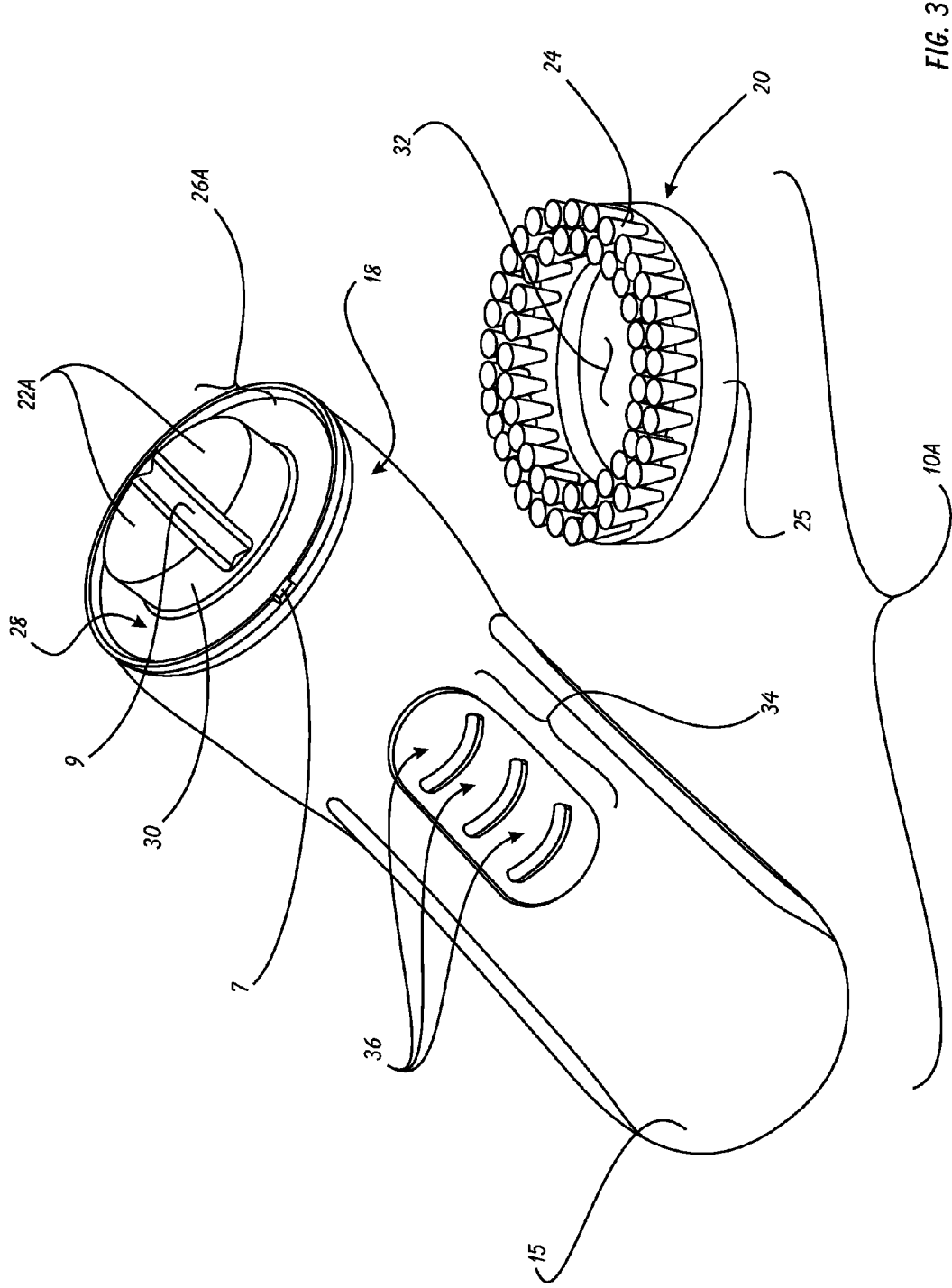
FIG. 3 is a partially exploded front perspective view of the device of FIGS. 1 and 2 having the detachable brush unit removed.

FIG. 2 is a rear perspective view of the device 10A of FIG. 1. As is shown clearly here, the handle section 14 and the head section 18 preferably interface to form an inverted "L" shape. The detachable brush unit 20 is defined by a plurality of tufts and/or bristles 24 extending forward from the face of the head section 18. As discussed previously, in order to improve the user's grip of the device 10A, a plurality of non-slip features, such as the grip pads 19A may be dispersed around the outer surface of the housing 12 (including on its rear face 17, although not shown here). These features prove to be particularly useful in view of the potential for the device 10A to be used while wet. FIG. 3 details additional structural and operational features of the present invention.

FIG. 3 is a partially exploded front perspective view of the device 10A of FIGS. 1 and 2 having the detachable brush unit 20 removed. As shown, the head section 18 terminates at its distal end in a doughnut-shaped head section face 28. Extending upwardly from the face 28 is the current emitter element 26A. The current emitter element 26A is defined by a continuous sidewall around its periphery, and terminates at its distal end in emitter face 22A. The emitter element 26A (and the associated circuitry within the housing 12) generates an electrical micro-current (the current at levels less than 1,000 microamperes) for application on the skin of the user. The device utilizes microcurrent technology to trigger the body's natural skin rejuvenation mechanism. The micro current emitted at the face 22A is created between two poles—negative and positive that define two "lobes" or halves of the current emitter element 26A. These lobes are separated from one another by insulation element 9, which is made from non-electrically-conductive material, such as plastic or rubber or the like. The insulation element 9 is formed with a groove the aesthetic qualities of the device head, as well as to aid in channeling lotions or other liquids or materials located on the user's skin while the emitter face 22A is being floated around on the user's skin surface.

In another (non-depicted) version of the design of the present invention, the conductor ridges 21 have been eliminated from the sides of the housing 12. Much like the version discussed below in connection with FIG. 4, this non-depicted version not include any metallic/conductive material for connection through the user's hand. For simplicity's sake, the negative and positive polarity necessary for generating the desired current emissions through the emitter face 22A will be provided by the emitter face 22A itself. For example, instead of providing negative polarity via the conductor ridges 21 on the sides of the housing 12, the negative pole could be the right lobe of the emitter face 22A. In this example, instead of the positive pole of the emitter circuitry being provided by both lobes of the emitter face 22A, it would instead be supplied by the left lobe of the emitter face 22A. It is even possible that the polarity of the two lobes of the face 22A could change back and forth in order to provide even emissions from both lobes of the face 22A (rather than isolating a single lobe as the emitter and the other lobe as the negative pole, for example).

Micro-current has two important functions during a facial treatment. Its main function is to introduce water-soluble products (lotions and other skin treatments) into the skin. Second, it is believed that the application of these localized micro-currents to the skin enhances the ability of these active molecules to penetrate the skin surface to increase the skin's absorption capacity, which works to minimize fine lines and wrinkles.

Microcurrent treatments such as this are safe for all skin types and all ages, and further are used and recommended by skin care professionals.

As effected by skin care professionals, a "microcurrent facelift" utilizes microcurrent technology (low level electrical current; 0-600 microamps for gentle electrical stimulation) to trigger the body's natural skin enhancement chemicals at a cellular level. It has been witnessed by some clinical studies that after twenty days of treatments, collagen production within the treated skin increased by 14%, elastin increased by 48%, and blood circulation increased by 38%.

Furthermore, followup testing after such treatments (as reported in a study) conducted at the University of Washington's Center of Pathology found a 45% increase in the number of elastin fibers in the dermis. Also impressive is the result that collagen thickness in connective tissue increased 10% and the number of blood vessels increased by 35%.

Still further, scientific evidence supports that microcurrent facelift treatments trigger the body's production of amino acids and ATP. Both of these accelerate cell repair and promote healthier cell production.

"The fact that this technology works in harmony with the body is evident . . . . The application of micro current to skin and tissue produced a firmer and tighter feeling on the skin surface."[1]

[1] Emil Y. Chi, PhD Director of the University of Washington's Department of Pathology The sidewall 30 may be configured in a slightly conical manner in order to facilitate the attachment and removal of the detachable brush unit 20. Alternatively, the sidewall 30 could be cylindrical, and the center aperture 32 could be cooperatively sized such as to prevent binding when the brush unit 20 is attached and detached from the head section of the device 10A.

The detachable unit 20 may attach/detach in a variety of optional manners, including snap-on/pull-off, twist-on/twist-off and slide-on/slide-off. The detachable unit 20 has a central aperture 32 formed through it to cooperatively accommodate the current emitter element, and allow it to protrude therethrough.

The conductors within the current emitter element 26A are made of chrome and copper. The materials for the conductor are electroplated metal over a plastic (e.g. ABS) core. In an alternate design, pure metal is used for these contacts.

As discussed previously, the conductor ridges 21 located on the sides of the housing (see FIGS. 1 and 2) are designed to be in contact with the user's hand when operating the device 10A/10B, in order to provide electrical conduction therebetween. The conductor ridges 21 serve as the negative poles to the positive polarity of the current emitter element in the head of the device. This arrangement provides the electrical polarity necessary for the current to flow from the current emitter element, through the user's body, and to the conductor ridges 21.

The front face 15 of the housing 12 is preferably formed with a plurality of buttons and/or visible indicators dispersed thereon. The mode control buttons 34 and indicator lights 36 allow the user to control, adjust and display the status of the various functional modes of the device 10A.

Figure 4:
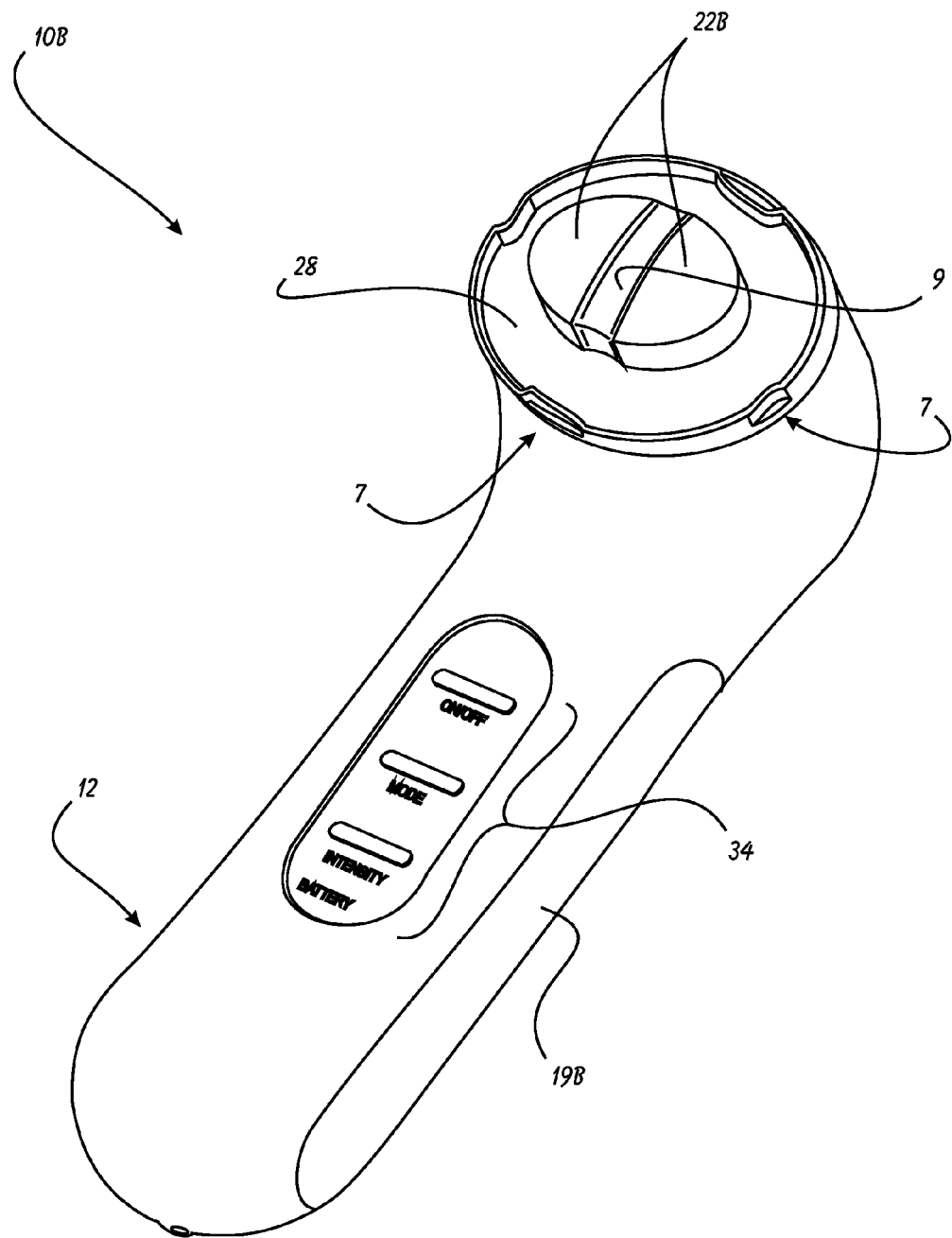
FIG. 4 is a front perspective view of a preferred embodiment of the handheld facial massage therapy device of the present invention.

FIG. 4 is a front perspective view of a preferred embodiment of the handheld facial massage therapy device of the present invention. The device 10B is essentially the same as the prior-discussed device (10A), except that it does not have micro-current generating capability. The emitter face 22B may appear to be identical to that of the device 10A, however, the internal circuitry of the device 10B does not generate micro-currents for emission at the emitter face 22B. Furthermore, it is possible that the conductor ridges (see FIG. 1) will not be located on the sides of the housing 12 (since there is no micro-current emission), and therefore the corresponding grip pads 19B would not have slots formed in them to expose the (non-existent) conductor ridges.

Figure 5:
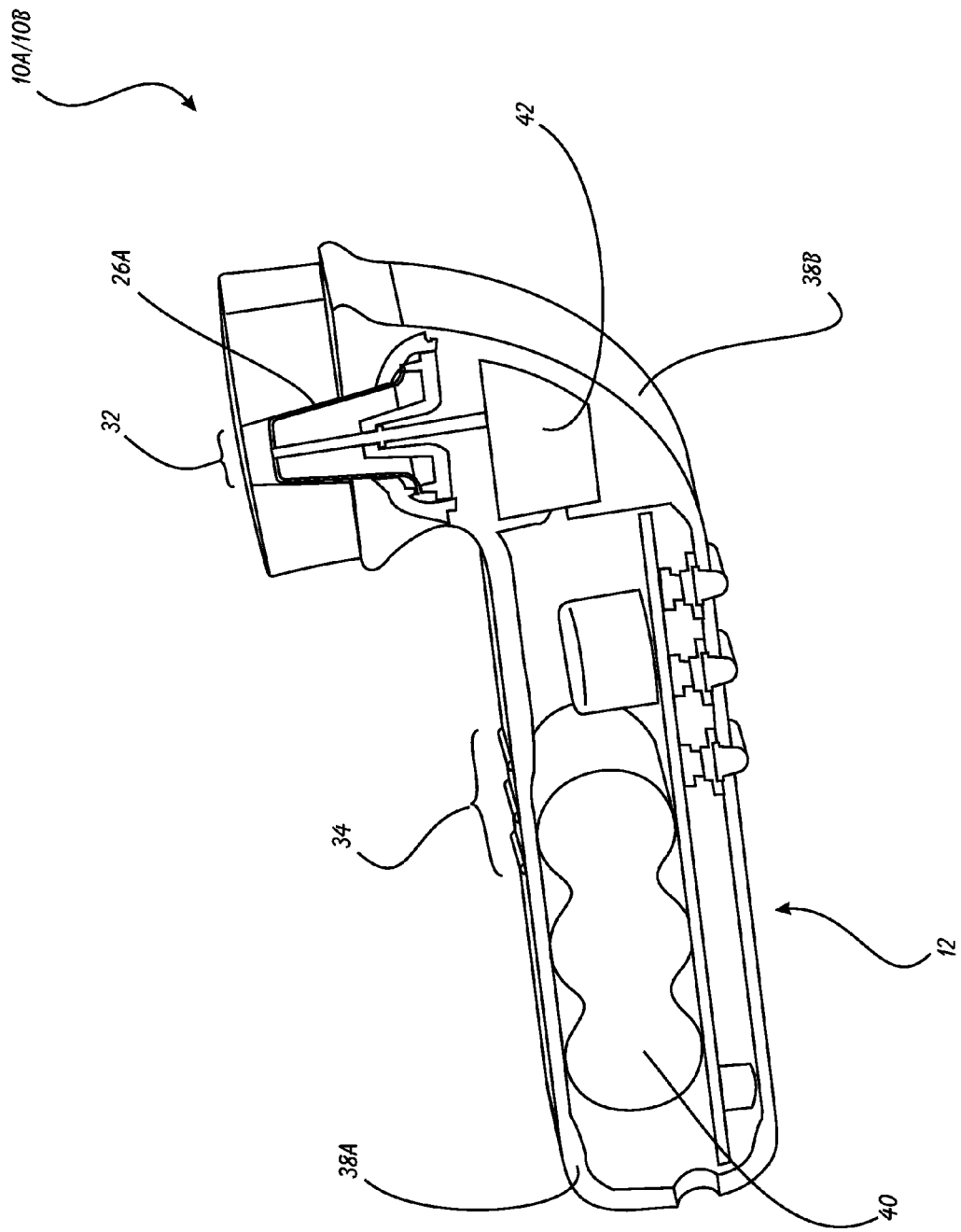
FIG. 5 is a cutaway side view of the device of FIGS. 1-4.

Also shown here are the interlock grooves 7 formed at spaced intervals around the periphery of the head section face 28. The grooves 7 are located to correspond to fingers or pegs formed on the back-side of the brush unit (20) so that the brush unit (20) twist-locks to attach (or detach) from the head section face 28. FIG. 5 depicts the pertinent internal components of the present invention.

FIG. 5 is a cutaway side view of the devices 10A and 10B of FIGS. 1-4. For the purposes of this drawing figure and the components discussed here, both devices 10A (having microcurrent emission capability) and 10B (absent micro-current generation) are equivalent.

The device 10A/10B preferably has a front housing half 38A attached to a rear housing half 38B with a water-resistant seal formed therebetween. Within the interior space formed in the housing 12, are the functional mechanisms or subsystems providing the functionality of the device 10A/10B. In general, there is a motor subassembly 42 and a battery pack 40 located within the housing 12. A micro-current generation subassembly is located in device 10A.

The mode control buttons and indicators 34 preferably protrude through or are otherwise dispersed on the front housing half 38A. The battery pack 40 could be a permanent rechargeable battery unit, or it could comprise one or more replaceable batteries.

While a variety of functional specifications are possible, it has been determined that the following specifications provide desirable results:
Impulse current at 10 vpp-25 vpp and 8-15 Hz in frequency
Motor size $\phi6$, $\phi10$, #130 to #260 motor sizes
Micro Current-Low level frequency range between 0.1 and 1,500 Hz At least two other embodiments are conceived herein:

A first alternative embodiment is termed "Transcutaneous electrical stimulator with limited output for aesthetic purposes," and produces limited power output in that it is intended for the home user. The operating ranges for the device output would be limited as prescribed by the U.S. Food and Drug administration under product code NYX:

a. Maximum Charge per phase: The device will emit a maximum charge per phase that does not exceed Q, where Q=20+(28)(t) microcoulombs (and where t is the phase duration expressed in milliseconds and measured at 50 percent of the phase amplitude);

b. Maximum current. The device will emit a maximum average current that does not exceed 10 milliamperes (average absolute value);

c. Depolarizing phase duration. The device will exhibit a maximum primary (depolarizing) phase duration that does not exceed 500 microseconds;

d. Average DC current. The device will emit an average DC current that does not exceed 100 microamperes when no pulses are being applied, or if the device fails;

e. Maximum current density. The device will emit a maximum current density that does not exceed 2 milliamperes r.m.s. per square centimeter of electrode conductive surface area (preferably 0.0522 mA r.m.s per square centimeter);

f. Maximum power density. The device will exhibit a maximum average power density that does not exceed 0.25 watts per square centimeter of electrode conductive surface area (preferably 0.00146 watts per square centimeter).

A second alternate embodiment may be termed "Transcutaneous Electrical Stimulator for Aesthetic Purposes," which is intended for professional treatment environments (however, which may be suitable for home use after sufficient testing has been accomplished). The operating ranges for the device output would be limited as prescribed by the U.S. Food and Drug administration under product code NFO:

a. Maximum Charge per phase: The device will emit a maximum charge per phase that may exceed Q, where Q=20+(28)(t) microcoulombs (and where t is the phase duration expressed in milliseconds and measured at 50 percent of the phase amplitude);

b. Maximum current. The device will emit a maximum average current that may exceed 10 milliamperes (average absolute value);

c. Depolarizing phase duration. The device will exhibit a maximum primary (depolarizing) phase duration that may exceed 500 microseconds;

d. Average DC current. The device will emit an average DC current that may exceed 100 microamperes when no pulses are being applied, or if the device fails;

e. Maximum current density. The device will emit a maximum current density that may exceed 2 milliamperes r.m.s. per square centimeter of electrode conductive surface area;

f. Maximum power density. The device will exhibit a maximum average power density that may exceed 0.25 watts per square centimeter of electrode conductive surface area.

Figure 6:
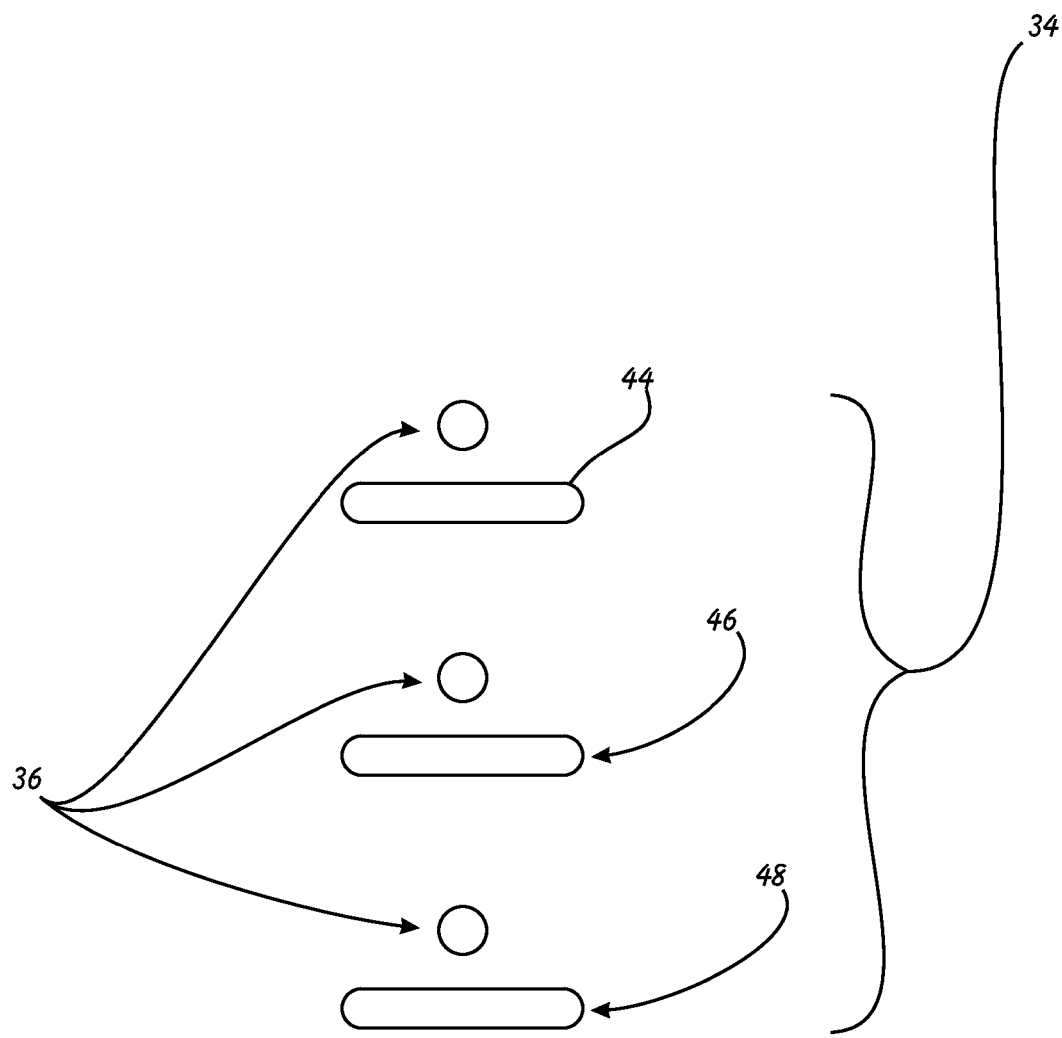
FIG. 6 depicts the mode control area of the device of FIGS. 1-3 and 5.

The user operational interface is discussed in connection with FIG. 6. FIG. 6 depicts the mode control area of the device 10A/B of FIGS. 1-3 and 5. While a wide variety of control features and configurations are conceived, the depicted version has been found to be convenient for all anticipated users. Where the term "button" is used herein, it is not intended to confine the disclosed design to a mechanical or electro-mechanical button, but rather is intended to include virtually any design for touch-sensitive switches intended for user interface (e.g. touchscreens, touchpads, switches, etc.).

The mode control buttons 34 will generally include at least the following elements: a main power button 44 for turning on and off the main power supply to the pulsating/vibrating and current-generating subassemblies. The vibration/pulse control button 46 enables the user to adjust the condition of the pulsating/vibrating movement generated by the motor subassembly (see FIG. 5). In its preferred form, the button 46 can be actuated to three distinct modes: off, on-low vibration/pulsing frequency, on-high vibration/pulsing frequency. The pulsing/vibrating of the motor subassembly (see FIG. 5) will cause the entire detachable brush unit (see FIG. 5) to agitate the user's skin when the brush is placed against it. This action will aid in the wet or dry cleansing/exfoliation of the skin in the treatment area.

The current emitter control button 48 can be pressed repeatedly to cycle from micro-current off condition, and through at least two more power levels (low and high) for micro-current generated at the emitter face (see FIG. 5).

There are preferably status lights 36, such as LED-type, that will convey to the user information related to battery status, pulsing/vibrating status and micro-current generation status. There is also a sound-generating subsystem associated with the control modes in certain embodiments. The sound-generating subsystem provides beeps or other audible prompts so as to provide the user with information regarding the operational condition of the device 10A/B.

Figure 7:
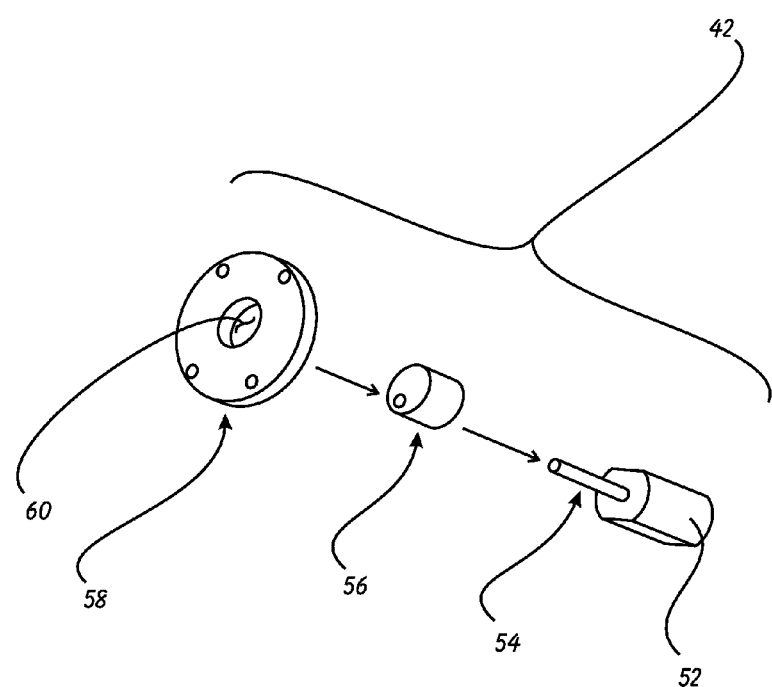
FIG. 7 is an exploded perspective view of the motor subassembly of the device of FIGS. 1-6.
Figure 8:
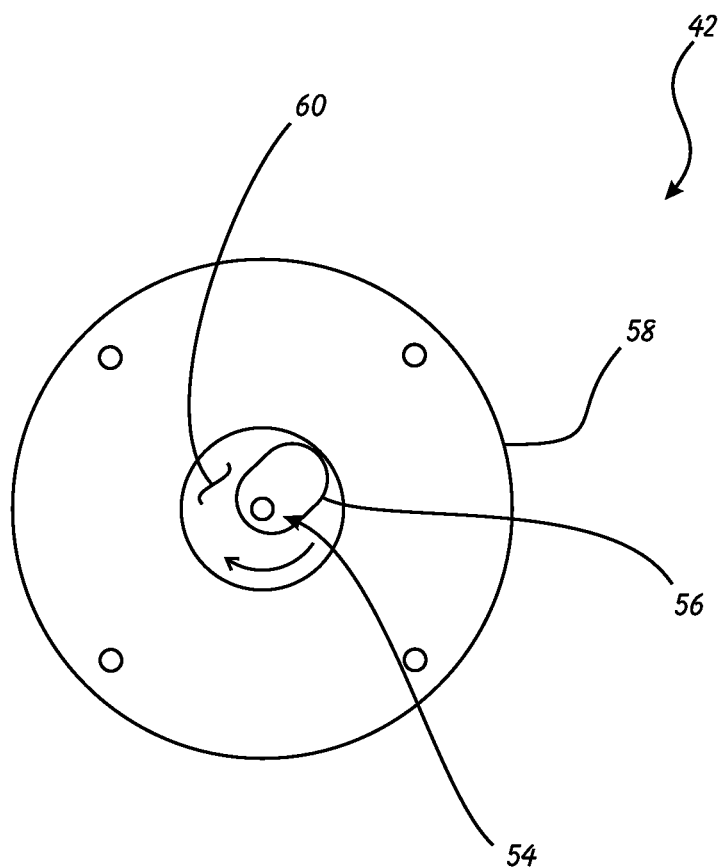
FIG. 8 is a front view of the motor subassembly of FIG. 7.

It is noted that a unique feature of this design is that the pulsing/vibrating action can be controlled independently from the micro-current generation, thereby allowing the user the flexibility to operate these two operational features simultaneously or separately. Furthermore, it should be apparent that the non-micro-current version of the instant invention would not include the current emitter control 48. FIGS. 7 and 8 provide additional detail regarding the mechanism responsible for creating the vibration/pulsing motion.

FIG. 7 is an exploded perspective view of the motor subassembly 42 of the device of FIGS. 1-6. The motor 52 has a rotating shaft 54 extending from it. An offset weight element 56 is pressed over the end of the shaft 54. When the shaft 54 turns (see arrow), it will cause the offset weight element 56 to also rotate. However, since the shaft 54 enters the offset weight element 56 at a distance from the element 56 center of gravity, the element 56 will "wobble" when it rotates. This "wobbling" will generate vibration in the handle of the device (to which the motor 52 is attached). A vibration transfer plate 58, which is defined by a weight interface aperture 60 formed therein, is mounted to the housing (12) such that the weight element 56 is located within the aperture 60. This protects the internal components of the device from accidental striking from the weight 56, and also may assist in the transfer of force from the weight element 56 to the housing sections.

Because there is no direct connection between the motor shaft 54 and the brush head (see FIG. 3), it is possible to create a sanitary seal between the face of the housing (see FIG. 3) and the internal workings of the device 10A/10B. The user is provided with the agitation/brushing/pulsing motion necessary to aid in the skin cleansing process, while also improving device cleanliness and also prolonging its reliability.

It should further be understood that in other embodiments, the motor shaft 54 may actually drive the brush unit 20, by mechanical linkage, to rotate, vibrate, oscillate or other movements. Of course, for such embodiments, the counter-weighted motor design depicted above in FIGS. 7 and 8 would not be appropriate. Instead, there would be an operable mechanism that interconnects the motor shaft 54 and the brush unit 20. In each of these cases, the current emitter element (or non-current-emitting emitter element) would remain stationary, and the brush unit 20 would rotate, oscillate, vibrate in relation thereto (and in relation to the housing 12).

FIG. 8 is a front view of the motor subassembly 42 of FIG. 7. As shown here, the motor shaft 54 penetrates the offset weight member 56 at an off-axis location. This causes the weight element 56 to create lateral forces when it is rotated. These lateral forces create the desired vibration/pulsing within the housing of the device.

Figure 9:
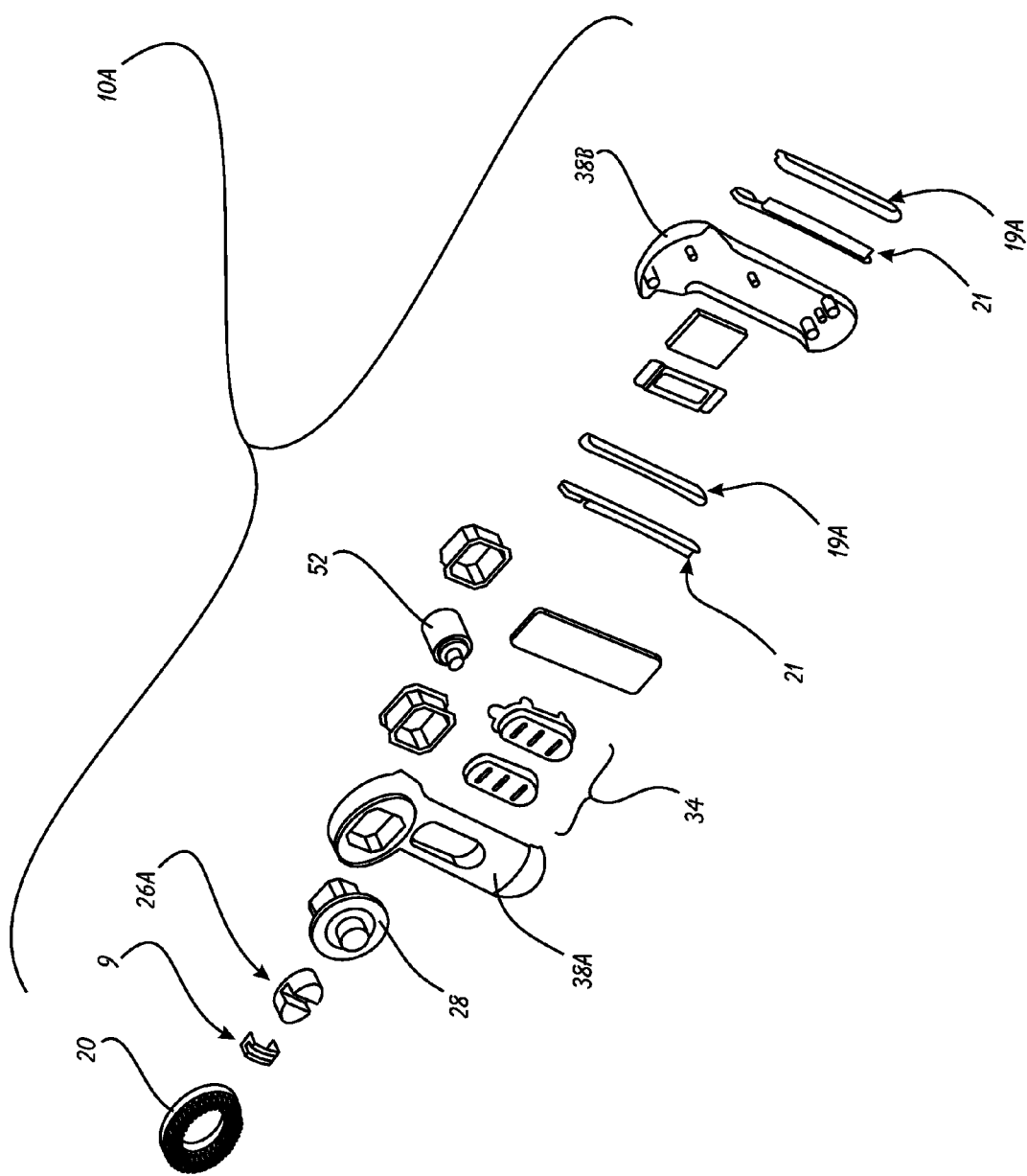
FIG. 9 is an exploded perspective view of the device of FIGS. 1-3.

FIG. 9 is an exploded perspective view of the device 10A of FIGS. 1-3. Each element making up the pair of conductor ridges 21 are located on opposing sides of the rear housing half 38B so that the user will easily have his or her hand/fingers in contact with them when normally grasping the device 10A for use. These conductor ridges 21 protrude through slots formed in the grasping pads 19A when the device 10A is fully assembled.

The current emitter element 26A is shown here detached from the face of the front housing half 38A. When fully assembled, the element 26A will be effectively integrated with the housing half 38A, however, it should be understood that the housing halves 38A, 38B are non-conductive, while the current emitter element 26A and conductor ridges 21 are metallic so that they will conduct electricity.

Figure 10:
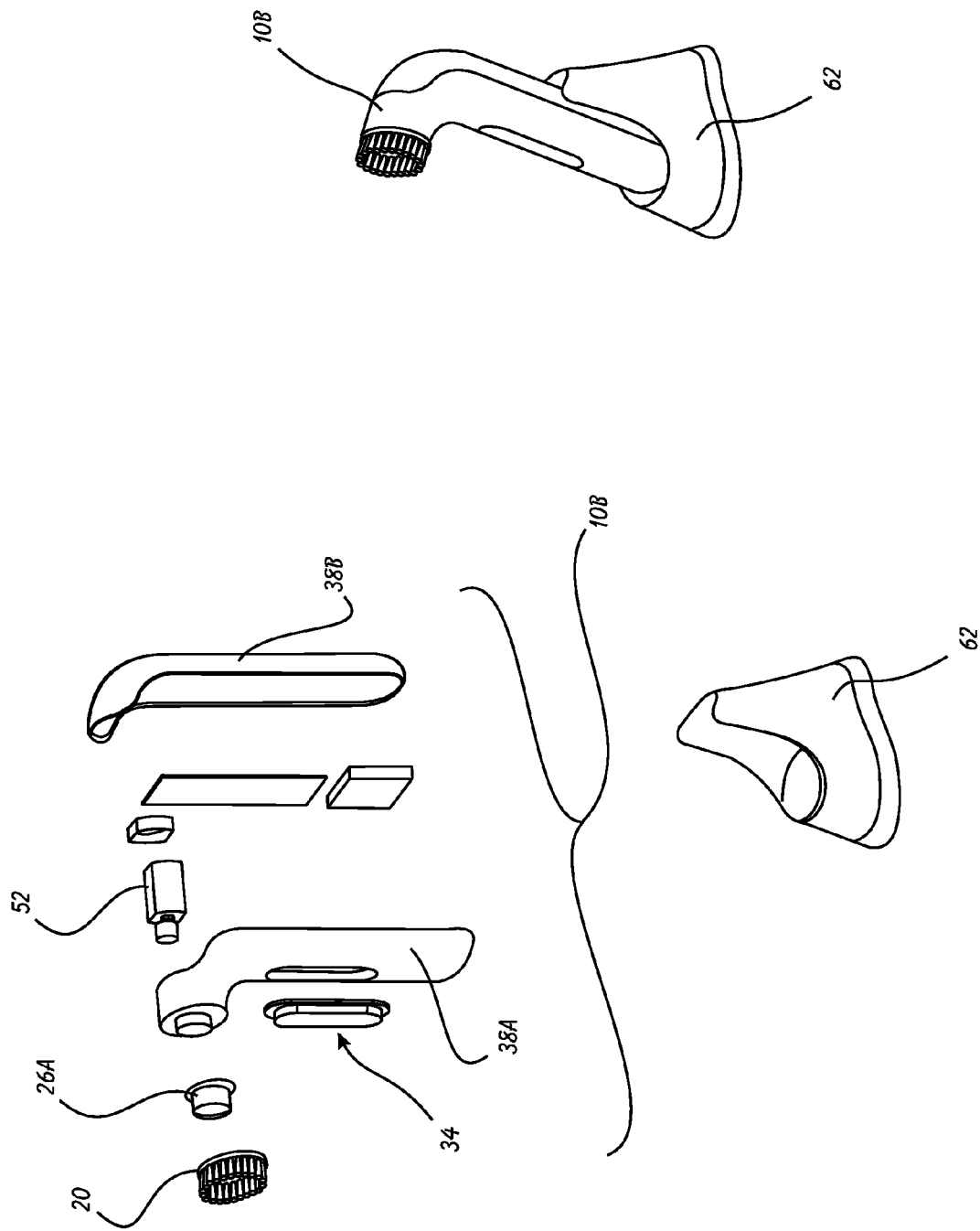
FIG. 10 is an exploded perspective view of the device of FIG. 4.

The device 10A shows one embodiment of the present invention, but it should be understood that other versions featuring other combinations of features and subsystems are conceived. For example, the present invention does include a device 10A that has the disclosed motor subassembly (see e.g. FIG. 7), but does not include the current-generating circuitry or external elements that has been described hereinabove. FIG. 10 is an exploded perspective view of the device of FIG. 4, wherein just such an alternate design is depicted.

The device 10B, from its outward appearance, is nearly identical to the micro-current-emitting version. Either device 10B or 10A is preferably paired with a charging base 62 that serves to provide safe countertop storage for the devices 10A/10B. Additionally, the base 62 is configured to be plugged into an electrical outlet for providing charging power to charge the internal batteries.

Summarizing the features and benefits of the present design, the device 10A/10B marries a motorized facial brush with micro-current technology to provide a non-invasive facelift with immediate results. Regular therapeutic use is expected to lift and tone the facial muscles and skin tissue. It is the innovation of providing professional technology that aestheticians can utilize. Therapy using the instant device is complimentary with other advanced professional treatments such as microdermabrasion, LED, oxygen, chemical peels, IPL and laser treatments. Other exemplary uses include:
   (1) pre and post operative care;
   (2) an "add-on" treatment to facials and other spa treatments; specialty treatment that lifts and tones the face, neck and body, and leaves skin feeling smoother and looking younger;
   (3) increases product (lotion, creams, treatments) penetration into the skin;
   (4) reduces the appearance of fine lines and wrinkles;
   (5) improves facial circulation;
   (6) improves skin appearance in case of hyper pigmentation, scars, pitting, blackheads and acne;
   (7) improved skin hydration and revitalization, resulting in smoother and softer skin;
   (8) decrease of puffiness and edema;
   (9) restoration of the "pink glow" of youthful tones;

(10) visible firming and contouring, lifting overall drooping features Tightening of sagging jowls, doubling chins, and fatty cheeks;

(11) the shrinking of enlarged pores;

(12) the reduction of dark circles and puffiness under eyes; and

(13) the reduction of the symptoms from Eczema, Melasma and Rosacea

Although not depicted herein, other functional modes/features are conceived of and may be provided in other embodiments of the present invention, including:

(a) Ultrasound/Ultrasonic

Low frequency sound waves 1 MHz+/−10% 1-10 MHz·Â at 1 MHz to 5 MHz range

High intensity in the 10 to 80 kHz range (b) Galvanic Current

Levels of the currents are 0.125 mA, 0.250 mA, 0.350 mA to 1.00 mA (milliamperes)

The purpose behind Galvanic is to utilize the flow of ions (electrons).

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A handheld facial massage device, comprising:

a housing sized for grasping by a human hand, said housing defined by a handle section and a head section extending therefrom;

a detachable massage unit attachable directly to said housing head section, said massage unit defined by a peripheral base from which extends one or more massage elements, said peripheral base having a central aperture formed therein, said massage elements each terminating in a distal end in spaced relation to said peripheral base; and an emitter element extending directly from said housing head section whereby when said massage unit is attached to said head section, a sidewall and an emitter face defined by said emitter element protrude through said central aperture of said peripheral base, such that said emitter face is in spaced relation to said peripheral base, and said emitter element sidewall is adjacent to said massage elements, said emitter face defined by a pair of metallic elements each terminating in a metallic face, said metallic faces separated by a non-metallic insulation element, wherein said insulation element defines a groove that is recessed relative to said metallic faces.

2. The device of claim 1, further comprising a motor subassembly located within said housing, said motor subassembly configured to generate vibrations within said housing that are perceptible at said massage unit.

3. The device of claim 2, wherein said massage unit, when attached to said head section, will not rotate or exhibit translational motion relative to said head section resulting from operation of said motor subassembly.

4. The device of claim 3, wherein said motor subassembly comprises:

an electric motor defined by a shaft driven to rotate by said motor;

an offset weight element attached to said shaft at a rotation point whereby a center of gravity defined by said offset weight element is in spaced relation to said rotation point; and a vibration transfer plate interconnecting said motor to said device housing.

5. The device of claim 4, wherein said one or more massage elements comprise brush bristle elements extending upwardly from said peripheral base.

6. The device of claim 4, wherein said one or more massage elements comprise a sponge element.

7. The device of claim 4, wherein said emitter element further comprises a generally cylindrical sidewall terminating in said face, said sidewall extending upwardly from said peripheral base a distance sufficient so that said face is approximately coplanar with said distal ends of said one or more massage elements.

8. The device of claim 7, further comprising:

a microcurrent subsystem located within said housing;

a pair of metallic conductor ridges protruding from opposing sides of said handle section, said one or more ridges operably electrically connectible to said microcurrent subsystem; and an electrically-conductive outer coating on said face of said emitter element, said face outer coating operably electrically connectible to said microcurrent subsystem.

9. The device of claim 2, wherein said motor subassembly is operatively connected to said detachable massage unit to operably generate relative movement between said detachable brush unit and said housing.

10. The device of claim 9, wherein said motor subassembly operably interconnects a motor shaft with said detachable massage unit whereby said relative movement is rotational in nature.

11. The device of claim 1, wherein said emitter element is generally circular in shape, and each said metallic element comprises substantially one-half of said generally circular shape.

12. A device for massaging a user's skin, comprising:

a housing less than four inches in diameter and less than eight inches in length so as to be graspable by a human hand, said housing defined by a handle section and a head section extending therefrom;

a detachable massage unit attachable directly to said housing head section, said massage unit defined by a peripheral base defined by a proximal wall and a distal wall, said proximal wall adjacent to said housing when said massage unit is attached thereto, with one or more massage elements defined by a proximal end extending from said distal wall, a body, and a distal end in spaced relation to said distal wall, said peripheral base having a central aperture formed therethrough; and an emitter element extending directly from said housing head section whereby when said massage unit is attached to said head section, a sidewall and an emitter face defined by said emitter element protrude through said massage unit central aperture, such that said body of said one or more massage elements is adjacent to said sidewall, said emitter element face comprising a pair of metallic elements in relative spaced relation and separated by a non-metallic insulation element, and wherein said insulation element defines an outer face that is recessed relative to the faces defined by said metallic elements.

13. The device of claim 12, further comprising a motor subassembly located within said housing, said motor subassembly configured to generate vibrations within said housing that are perceptible at said massage unit.

14. The device of claim 13, wherein said motor subassembly comprises:
an electric motor defined by a shaft driven to rotate by said motor;
an offset weight element attached to said shaft at a rotation point whereby a center of gravity defined by said offset weight element is in spaced relation to said rotation point; and
a vibration transfer plate interconnecting said motor to said device housing.

15. The device of claim 14, wherein said emitter element comprises a sidewall terminating in a face, said sidewall extending upwardly from said peripheral base to a distance sufficient so that said face is approximately coplanar with a a distal face defined by said one or more massage elements.

16. The device of claim 15, further comprising:
a microcurrent subsystem located within said housing; and
an electrically-conductive outer coating on said face of said emitter element, said face outer coating operably electrically connectible to said microcurrent subsystem.

17. The device of claim 12, wherein said motor subassembly operably interconnects a motor shaft with said detachable massage unit to generate relative movement between said massage unit and said housing, with said relative movement being rotational in nature.

18. A method for rejuvenating a user's skin, comprising the steps of:
manipulating the user's skin by placing a handheld device against the user's skin, wherein said handheld device comprises:
a housing less than four inches in diameter and less than eight inches in length so as to be graspable by a human hand, said housing defined by a handle section and a head section extending therefrom;
a detachable massage unit attached directly to said head section, said massage unit defined by a peripheral base from which extends one or more massage elements, said peripheral base having a central aperture formed therethrough, said massage elements each terminating in a distal end in spaced relation to said peripheral base; and
an emitter element extending directly from said head section whereby a sidewall and an emitter face defined by said emitter element protrude through said central aperture of said peripheral base, such that said emitter face is in spaced relation to said peripheral base, and said emitter element sidewall is adjacent to said massage elements, said emitter face defined by a pair of metallic elements separated by a non-metallic insulation element, wherein said non-metallic insulation element forms a recessed groove between said metallic elements;
whereby said placing step comprises simultaneously placing said one or more massage elements and said emitter element against the user's skin.

19. The method of claim 18, wherein said placing step comprises placing said massage elements and said emitter element against the user's skin, with said handheld device further comprising:
an electric motor defined by a shaft driven to rotate by said motor;
an offset weight element attached to said shaft at a rotation point whereby a center of gravity defined by said offset weight element is in spaced relation to said rotation point; and
a vibration transfer plate interconnecting said motor to said device housing.

20. The method of claim 18, wherein said placing step comprises placing said massage elements and said emitter element against the user's skin, with said handheld device further comprising:
a microcurrent subsystem located within said housing; and
an electrically-conductive outer coating on said face of said emitter element, said face outer coating operably electrically connectible to said microcurrent subsystem.

\* \* \* \* \*